(12) United States Patent
Hines

(10) Patent No.: US 9,050,034 B1
(45) Date of Patent: Jun. 9, 2015

(54) APPARATUS AND METHOD FOR MONITORING THE CONDITION OF A NIGHT VISION DEVICE USER WITH NON-VISIBLE LIGHT

(71) Applicant: EXELIS, INC., McLean, VA (US)

(72) Inventor: Kevin P. Hines, Daleville, VA (US)

(73) Assignee: EXELIS, Inc., McLean, VA (US)

( * ) Notice: Subject to any disclaimer, the term of this patent is extended or adjusted under 35 U.S.C. 154(b) by 297 days.

(21) Appl. No.: 13/777,054

(22) Filed: Feb. 26, 2013

(51) Int. Cl.
*A61B 3/14* (2006.01)
*A61B 3/00* (2006.01)
*A61B 3/113* (2006.01)

(52) U.S. Cl.
CPC ...................................... *A61B 3/113* (2013.01)

(58) Field of Classification Search
USPC .................................. 351/206, 209, 210, 246
See application file for complete search history.

(56) References Cited

U.S. PATENT DOCUMENTS

2011/0077548 A1    3/2011    Torch

*Primary Examiner* — Jack Dinh
(74) *Attorney, Agent, or Firm* — RatnerPrestia

(57) ABSTRACT

A system for monitoring the condition of an optical device user with non-visible light includes a non-visible light source that is positioned to direct a beam of non-visible light onto an eye of the optical device user. A non-visible light sensor is positioned to receive non-visible light that is reflected off of the eye and is configured to generate a signal corresponding to either a level or an intensity of the received non-visible light. A processor is connected to the light sensor, and is configured to determine a condition of the eye including whether the eye is either not moving, closed without blinking or open without blinking for more than a pre-determined amount of time based upon signals received from the light sensor. Also disclosed herein is a method for monitoring the condition of an optical device user with non-visible light.

20 Claims, 2 Drawing Sheets

APPARATUS AND METHOD FOR MONITORING THE CONDITION OF A NIGHT VISION DEVICE USER WITH NON-VISIBLE LIGHT

FIELD OF THE INVENTION

This invention relates to an apparatus and a method for monitoring the condition of an optical device user with non-visible light.

BACKGROUND OF THE INVENTION

A night vision goggle (NVG), which is well known in the art, is an optical device that allows images to be produced in levels of light approaching total darkness. NVG's are most often worn by the military and law enforcement personnel, whose health and safety are of the utmost importance.

The present invention is directed to apparatus, systems, and methods for monitoring movement of one or more eyes, eyelids, and/or pupils of an NVG user. Monitoring the eye movement of the NVG user is useful in determining whether that NVG user is either unconscious or incapacitated, and therefore requires assistance.

As described in U.S. Patent App. Pub. No. 2011/0077548 to Torch, which is incorporated by reference herein in its entirety, humans blink at least about 5-30 times per minute. Each involuntary-reflexive blink lasts about 200-300 milliseconds, generally averaging about 250 milliseconds. As tiredness or sleepiness occurs, the eye blink may get longer and slower and/or the blink rate may vary, and/or the eyelids may begin to droop with small amplitude eye lid blinks, e.g., until the eyes begin to close for short term "microsleeps," i.e., sleep conditions that last for about 3-5 seconds or longer, or for prolonged sleep.

Furthermore, the pupils may constrict more sluggishly, show unstable fluctuations in size, shrinking progressively in diameter, and/or demonstrate delayed responses to light flashes (i.e. delayed pupil response latency) as sleepiness and fatigue progresses. In addition, other ocular manifestations of drowsiness may occur, such as slow or delayed saccadic eye tracking responses, e.g., to a stimulus (i.e., delayed saccadic response latency), with either over- or under-shooting the target, and/or a loss of directed gaze with or without binocular vergence or divergence, eye drift, or esophoria.

Thus, monitoring the movement of one or more eyes, eyelids, and/or pupils of an NVG user would help determine whether that user requires immediate assistance.

SUMMARY OF THE INVENTION

According to one aspect of the invention, a system for monitoring a night vision goggle user with non-visible light comprises a non-visible light source that is positioned to direct a beam of non-visible light onto an eye of the night vision goggle user; a non-visible light sensor that is positioned to receive non-visible light that is reflected off of the eye and is configured to generate a signal corresponding to either a level or an intensity of the received non-visible light; and a processor that is connected to the light sensor, and is configured to determine a condition of the eye including whether the eye is either not moving, closed without blinking or open without blinking for more than a pre-determined amount of time based upon signals received from the light sensor.

According to another aspect of the invention a night vision goggle comprises a lens through which a user of the night vision goggle views a scene; a non-visible light source that is positioned adjacent the lens and is positioned to direct a beam of non-visible light onto an eye of the night vision goggle user; a non-visible light sensor that is positioned adjacent the lens and is positioned to receive non-visible light that is reflected off of the eye, the non-visible light sensor being configured to generate a signal corresponding to either a level or an intensity of the received non-visible light; and a processor that is connected to the light sensor, and is configured to determine a condition of the eye including whether the eye is either not moving, closed without blinking or open without blinking for more than a pre-determined amount of time based upon signals received from the light sensor.

According to yet another aspect of the invention, a method for monitoring a condition of a night vision goggle user with non-visible light comprises the steps of: directing non-visible light onto an eye of the night vision goggle user; sensing non-visible light reflected off of the eye; generating a signal corresponding to either an intensity or a level of the reflected non-visible light; and transmitting an alert if a level of the signal remains constant for more than a pre-determined amount of time to indicate that the user is either incapacitated or unconscious.

BRIEF DESCRIPTION OF THE DRAWING FIGURES

The invention is best understood from the following detailed description when read in connection with the accompanying drawing. Included in the drawing are the following figures.

DETAILED DESCRIPTION OF THE DRAWING FIGURES

The invention is best understood from the following detailed description when read in connection with the accompanying drawing figures, which shows exemplary embodiments of the invention selected for illustrative purposes. The invention will be illustrated with reference to the figures. Such figures are intended to be illustrative rather than limiting and are included herewith to facilitate the explanation of the present invention.

Figure 1:
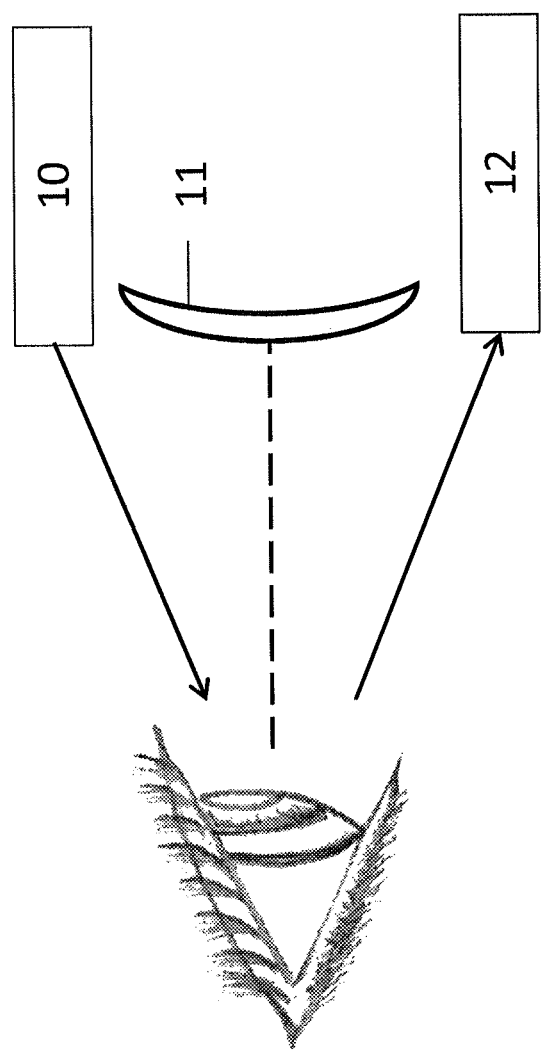
FIG. 1 is a schematic diagram depicting a non-visible light source emitting non-visible light onto a surface of a user's eye and a light sensor receiving the reflected non-visible light, according to one exemplary embodiment of the invention.
Figure 2:
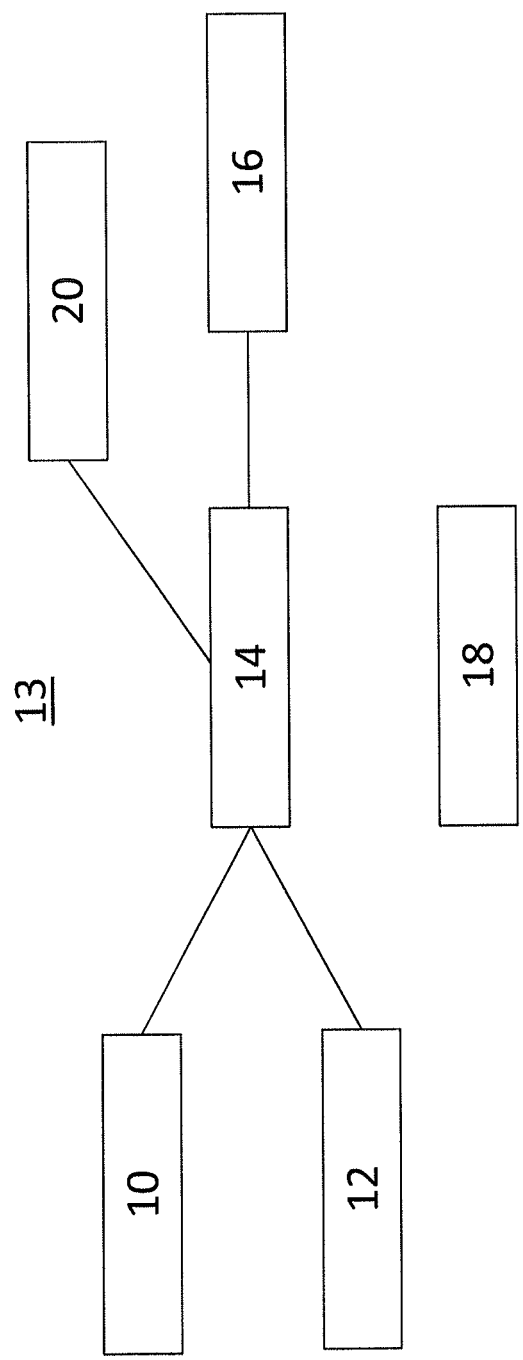
FIG. 2 depicts a schematic diagram of a system for monitoring a night vision goggle user with non-visible light, according to one exemplary embodiment of the invention.

Referring to FIG. 1, that figure is a schematic diagram depicting a non-visible light source 10 emitting non-visible light onto a surface of a user's eye and a non-visible light sensor 12 for sensing the reflected non-visible light, according to one exemplary embodiment of the invention. FIG. 2 depicts a schematic diagram of a system 13 for monitoring a night vision goggle user with non-visible light, according to one exemplary embodiment of the invention.

The system 13 generally includes the non-visible light source 10 and the non-visible light sensor 12 of FIG. 1, a processor 14, a transmitter 16, a power source 18 and an optional discrete (on/off) sensor 20.

Specifically, the non-visible light source 10 is connected to the processor 14. The light source 10 is mounted either directly or indirectly to the NVG, such that it is positioned in close proximity to the lens 11 of the NVG and the eye of the NVG user. The user's line of sight is represented by a broken line in FIG. 1. The light source 10 is configured to emit non-visible light onto the eye. The light source 10 emits light having any wavelength that is non-destructive to the human eye. The wavelength of the light emitted by the light source 10 may vary. The light source 10 may be infrared, near infrared, or short-wavelength infrared, for example. According to one embodiment of the invention, the light source 10 is a commercially available infrared LED having a wavelength of 880 nm, for example.

The non-visible light sensor 12 is connected to the processor 14. The light sensor 12 is mounted either directly or indirectly to the NVG, such that it is positioned in close proximity to the lens 11 of the NVG and the eye of the NVG user. The non-visible light sensor 12 is configured to sense the reflected non-visible light and transmit a signal corresponding to either the level or the intensity of the sensed light. Specifically, the reflected light is modulated as the user moves his eye, and this modulated reflectance (in the form of light) is measured by the light sensor 12. The light sensor 12 is capable of converting the sensed light into either a current signal or a voltage signal, depending upon its mode of operation. If the user's blinks or moves his or her eye, then the current or voltage signal will fluctuate. Alternatively, if the user's eye is closed, open or not moving, then the current or voltage signal will be substantially constant. The light sensor 12 may be a commercially available infrared sensor, such as a photo detector. The photo detector may be a photo transistor or a photo diode.

The discrete (on/off) sensor 20 is activated when the user places the NVG on his or her head. The discrete sensor 20 is deactivated when the user removes the NVG from his head. The discrete sensor 20 may be a commercially available pushbutton switch, for example. The sensor 20 is also connected to the processor 14.

The processor 14 is generally configured to (i) either monitor or activate the light source 10, (ii) receive and analyze signals from the sensor 20 to determine if the NVG is being worn by the user, (iii) receive and analyze signals from the light sensor 12 to determine the condition of the user's eye, and (iv) transmit a signal to the transmitter 16 if the NVG is being worn by the user and the user's eye is closed, open or not moving for a pre-determined amount of time. Upon receiving a signal from the processor 14, the transmitter 16 is configured to transmit a warning signal indicating that the user of the NVG device requires assistance because the user is either unconscious or incapacitated. The processor 14 and the transmitter 16 are commercially available.

The light source 10, the light sensor 12, the processor 14, the transmitter 16 and the optional sensor 20 are powered by a power source 18. The power source 18 may be a separate battery pack, or the power source 18 may be the power source of the NVG.

The system 13 may be integrated with the night vision goggle, or it may be retrofitted thereto.

In operation, the NVG is activated and the user places the NVG on his or her head. The sensor 20 senses that the NVG is in use and transmits a signal to the processor. The sensor 20 prevents false warnings that could occur when the system 13 is activated but a user is not wearing the NVG.

The processor 14 either monitors or activates the light source 10. The non-visible light source 10 emits non-visible light onto a surface of a user's eye. The light source 10 emits non-visible light either continuously, periodically or on demand. The non-visible light reflects off of the surface of the user's eye, and either the level or the intensity of the reflected light is sensed and measured by the light sensor 12 and the light sensor 12 produces an electrical signal. Specifically, as the user moves his eye or blinks the reflected light is modulated. This modulated reflectance is sensed and measured by the light sensor 12 and then communicated to the processor 14 in the form of an electrical signal.

The processor 14, in turn, analyzes the electrical signal sent by the light sensor 12 and determines whether the light source 10 is activated. According to one exemplary embodiment, if the light source 10 is activated and the level of the reflected signal is substantially constant for more than a pre-determined amount of time, indicating that the user's eye is either closed without blinking, open without blinking or not moving for an extended period of time, then the processor 14 transmits a signal to the transmitter 16. If the system 13 includes a sensor 20, then the processor 14 transmits a signal to the transmitter 16 only if the processor 14 determines that the sensor 20 is activated (i.e., indicating that the NVG is being worn by a user).

The transmitter 16, in turn, wirelessly transmits a warning signal indicating that the user of the NVG device requires assistance because the user is either unconscious or incapacitated. The transmitter 16 may be replaced with a warning light attached to the NVG or a speaker attached to the NVG that transmits an audible warning message.

According to one aspect of the invention, the pre-determined amount of time is approximately sixty seconds. According to another aspect of the invention, the pre-determined amount of time is approximately thirty seconds. It should be understood that the pre-determined amount of time can vary.

The system of FIG. 2 could also incorporate accelerometers, gyroscopes, and cameras to detect motion of the NVG user or the lack thereof. Such solutions may be useful as a back-up to the light sensor 12. However, accelerometers and gyroscopes are complex and may be susceptible to damage due to shock loads, and the failure of either of those components could cause the entire system to fail. And, camera systems need to maintain focus, and if defocused, may not operate properly. Additionally, it could be difficult to integrate or retrofit accelerometers, gyroscopes, and cameras into the NVG.

While preferred embodiments of the invention have been described herein, it will be understood that such embodiments are provided by way of example only. Numerous variations, changes and substitutions will occur to those skilled in the art without departing from the spirit of the invention. It is intended that the appended claims cover all such variations as fall within the spirit and scope of the invention.

What is claimed:

1. A system for monitoring the condition of an optical device user with non-visible light, comprising:
    a non-visible light source that is positioned to direct a beam of non-visible light onto an eye of the optical device user;
    a non-visible light sensor that is positioned to receive non-visible light that is reflected off of the eye and is configured to generate a signal corresponding to either a level or an intensity of the received non-visible light; and
    a processor that is connected to the light sensor, and is configured to determine a condition of the eye including whether the eye is either not moving, closed without blinking or open without blinking for more than a pre-determined amount of time based upon signals received from the light sensor.

2. The system of claim 1, wherein the processor is also connected to the non-visible light source and is configured to either control activation or monitor activation of the light source.

3. The system of claim 1, wherein the processor is configured to determine whether the eye is either not moving, closed or open only when the non-visible light source is activated.

4. The system of claim 1 further comprising a transmitter that is connected to the processor, wherein when the processor determines that the eye is either not moving, closed or open for more than a pre-determined amount of time, the processor is configured to transmit a signal to the transmitter, and the transmitter is configured to transmit a signal to alert others to the condition of the eye.

5. The system of claim 1 further comprising the optical device, wherein the light sensor and the light source are associated with the optical device.

6. The system of claim 1, wherein the pre-determined amount of time is one minute.

7. The system of claim 1, wherein a wavelength of the non-visible light produced by the light source is infrared, near infrared, or short-wavelength infrared.

8. The system of claim 1 further comprising a discrete sensor that is activated when the user is wearing the optical device, wherein the discrete sensor is connected to the processor, and the processor is configured to determine the condition of the eye only when the discrete sensor is activated.

9. The system of claim 1, wherein the non-visible light sensor is a photo detector.

10. An optical device comprising:
   a lens through which a user of the optical device views a scene;
   a non-visible light source that is positioned adjacent the lens and is positioned to direct a beam of non-visible light onto an eye of the optical device user;
   a non-visible light sensor that is positioned adjacent the lens and is positioned to receive non-visible light that is reflected off of the eye, the non-visible light sensor being configured to generate a signal corresponding to either a level or an intensity of the received non-visible light; and
   a processor that is connected to the light sensor and is configured to determine a condition of the eye including whether the eye is either not moving, closed without blinking or open without blinking for more than a pre-determined amount of time based upon signals received from the light sensor.

11. The optical device of claim 10, wherein the processor is also connected to the non-visible light source and is configured to either control activation or monitor activation of the light source.

12. The optical device of claim 10, wherein the processor is configured to determine whether the eye is either not moving, closed or open only when the non-visible light source is activated.

13. The optical device of claim 10 further comprising a transmitter that is connected to the processor, wherein when the processor determines that the eye is either not moving, closed or open for more than a pre-determined amount of time, the processor is configured to transmit a signal to the transmitter, and the transmitter is configured to transmit a signal to alert others to the condition of the eye.

14. The optical device of claim 10, wherein the pre-determined amount of time is one minute.

15. The optical device of claim 10, wherein a wavelength of the non-visible light produced by the light source is infrared, near infrared, or short-wavelength infrared.

16. The optical device of claim 10, further comprising a discrete sensor that is activated when the user is wearing the optical device, wherein the discrete sensor is connected to the processor, and the processor is configured to determine the condition of the eye only when the discrete sensor is activated.

17. The optical device of claim 10, wherein the non-visible light sensor is a photo detector.

18. A method for monitoring the condition of an optical device user with non-visible light, comprising the steps of:
   directing non-visible light onto an eye of the optical device user;
   sensing non-visible light reflected off of the eye;
   generating a signal corresponding to either an intensity or a level of the reflected non-visible light; and
   transmitting an alert if a level of the signal remains constant for more than a pre-determined amount of time to indicate that the user is either incapacitated or unconscious.

19. The method of claim 18, wherein the pre-determined amount of time is less than one minute.

20. The method of claim 18 further comprising the step of determining whether the optical device is being worn by the user, and wherein the transmitting step is carried out only if the determining step indicates that the optical device is being worn by the user.

* * * * *